(12) United States Patent
Palmisano

(10) Patent No.: US 6,536,439 B1
(45) Date of Patent: Mar. 25, 2003

(54) APPARATUS AND METHODS FOR TREATMENT OF CONDITIONS INCLUDING OBSTRUCTIVE SLEEP APNEA AND SNORING

(76) Inventor: Richard George Palmisano, 8/9 Guilfoyle Ave., Double Bay, New South Wales 2028 (AU)

(*) Notice: Subject to any disclaimer, the term of this patent is extended or adjusted under 35 U.S.C. 154(b) by 0 days.

(21) Appl. No.: 08/941,518

(22) Filed: Sep. 30, 1997

Related U.S. Application Data

(63) Continuation of application No. PCT/AU96/00187, filed on Apr. 1, 1996.

(30) Foreign Application Priority Data

Mar. 30, 1995 (AU) .............................................. PN2057

(51) Int. Cl.[7] .................................................. A61F 5/56
(52) U.S. Cl. ....................................................... 128/848
(58) Field of Search ................................ 128/846, 848, 128/859–862; 602/902; 433/3, 2, 4, 5, 7, 18, 24, 141, 152, 153, 157, 159, 162; 81/52

(56) References Cited

U.S. PATENT DOCUMENTS

| | | | |
|---|---|---|---|
| 4,144,643 A | 3/1979 | Krygier | 32/14 E |
| 4,197,644 A | 4/1980 | Ackerman, Jr. | 433/7 |
| 4,507,084 A | 3/1985 | Blechman et al. | 433/7 |
| 4,901,737 A | 2/1990 | Toone | 128/848 |
| 5,133,659 A | 7/1992 | Shilliday | 433/433 |
| 5,313,960 A | 5/1994 | Tomasi | 128/848 |

OTHER PUBLICATIONS

Donald J. Timms, "Rapid Maxillary Expansion", Quintessence Publishing Co., Inc., Chicago, Illinois, Chapter III, pp. 27–46 (1981).

Lindsay P. Gray, "Results of 310 cases of rapid maxillary expansion selected for medical reasons", *The Journal of Laryngology and Otology*, Headley Brothers, Ltd., England, vol. 89, pp. 601–614 (1975).

*Primary Examiner*—Michael A. Brown
(74) *Attorney, Agent, or Firm*—Townsend and Townsend and Crew LLP

(57) ABSTRACT

Apparatus and methods for the treatment of conditions including obstructive sleep apnea and/or snoring resulting from excessive nasal airway resistance are disclosed. A rapid maxillary expansion device (10) is fitted to teeth (12, 14) of the upper jaw, and by operation of the jack screw (20), the maxilla is expanded such that, usually, the intermaxillary suture opens. The expansion is maintained until the maxilla stabilizes, for example by new bone growth along the suture. In this way the minimum cross-sectional area of the nasal cavity increases, reducing nasal airway resistance and curing, or at least ameliorating, obstructive sleep apnea and/or snoring.

24 Claims, 5 Drawing Sheets

APPARATUS AND METHODS FOR TREATMENT OF CONDITIONS INCLUDING OBSTRUCTIVE SLEEP APNEA AND SNORING

This application is a continuation of PCT/AU96/00187 with an international filing date of Apr. 1, 1996.

FIELD OF THE INVENTION

This invention relates to apparatus and methods for the treatment of conditions including obstructive sleep apnea (OSA) and snoring. The invention is believed also to relate to the treatment of other upper respiratory conditions.

BACKGROUND OF THE INVENTION

OSA is the medical condition where the airway becomes partially or fully occluded during sleep in the region of the oro- or hypopharynx. It is a progressive condition that is recognised amongst middle or older aged overweight men, although it is by no means uncommon amongst women and younger people, including adolescents, children and infants. There have been many papers published discussing the medical consequences of OSA and associated syndromes on a person's well being. The pathophysiological cause of OSA remains the subject of some dispute.

The preferred clinical treatment for OSA is Continuous Positive Airway Pressure (CPAP) which acts to alleviate the occurrence of apneas and hypopneas during sleep. CPAP is the technique of pneumatically splinting the airway open by supplying air at a pressure elevated above atmospheric pressure to the nose, or to the nose and mouth. It is not, however, a curative treatment.

Surgical techniques are also known, however they are radical treatments that have generally been disappointing as a curative.

DISCLOSURE OF THE INVENTION

The inventor, a specialist orthodontist, believes a root cause of OSA can be maxillary constriction leading to excessive or increased nasal airway resistance and mouth breathing, necessitating mouth opening. Maxillary constriction is but one cause of excessive nasal airway resistance. Both this and the low tongue position, associated with the narrowness of the hard palate, result in further postural changes and airway obstruction, leading to snoring and with swallowing problems, to sleep apnea.

The inventor further believes conditions such as certain forms of asthma and upper respiratory tract infections can be attributed to or exacerbated by reduced nasal air conditioning, mouth breathing and low tongue position caused by increased nasal airway resistance. Further, swallowing problems can be attributed to excessive mouth breathing consequent to increased nasal airway resistance, resulting in postural changes. Yet further, cot death can be attributed to postural changes caused by increased nasal airway resistance, resulting in swallowing difficulties. These are conditions that hitherto have not been connected with mouth breathing caused by increased nasal airway resistance.

FIG. 1 is a flow diagram of the progression and interrelationships leading to snoring and sleep apnea from maxillary constriction.

The nasal airway is to be understood as the airway formed between the choanae and the nares.

It is an object of the invention to provide a curative, or at least an ameliorative treatment for conditions including OSA and snoring resulting from excessive nasal airway resistance.

The present invention discloses a method for the treatment of obstructive sleep apnea and/or snoring resulting from maxillary constriction, the method comprising the steps of:

identifying an individual that suffers from at least one condition selected from the group consisting obstructive sleep apnea and snoring;

separating the intermaxillary suture of the individual; and maintaining the separation until a gap formed thereby is occupied by new bone growth and an intermaxillary suture is reformed, resulting in an increased nasal airway volume and hence a reduction of nasal airway resistance.

The invention further discloses a method for the treatment of obstructive sleep apnea and/or snoring comprising the steps of:

identifying an individual that suffers from at least one condition selected from the group consisting obstructive sleep apnea and snoring;

securing an expansion device to cause orthopaedic displacement of the opposed sides of the upper jaw of the individual to achieve separation of the intermaxillary suture; and maintaining the separation until the gap formed thereby is occupied by new bone growth and an intermaxillary suture is reformed.

Advantageously, the method further comprises the step of surgically performing a partial corticotomy of the buccal surfaces of the maxillae with or without extension to the piriform aperture or the pterygomaxillary fissure in conjunction with the step of expanding.

Preferably, the expansion device is secured to one or more of the posterior teeth on opposed sides of the upper jaw.

The invention further discloses an implement when used for the treatment of obstructive sleep apnea and/or snoring resulting from excessive nasal airway resistance, the implement comprising means for attachment to the posterior upper jaw at opposed locations and means for causing orthopaedic movement of the upper jaw to cause separation of the intermaxillary suture, and means for maintaining the separation until a stable intermaxillary suture is formed, thereby reducing nasal airway resistance.

Preferably, the attachment means is releasably engageable with the upper jaw. In one preferred form the attachment means secure to one or more of the teeth. In a yet further preferred form the implement is a rapid maxillary expansion device.

The invention further discloses a method for the treatment of the adverse pathophysiological effects of mouth breathing resulting from maxillary constriction, the method comprising the steps of:

expanding the maxilla; and maintaining the maxillary expansion until a stable state of the maxilla is established.

The invention yet further discloses a method for the treatment of obstructive sleep apnea and/or snoring comprising the steps of:

identifying an individual that suffers from at least one condition selected from the group consisting obstructive sleep apnea and snoring;

laterally expanding the maxillae of the individual; and maintaining the maxillary expansion until a stable state of the maxilla is established.

The invention yet further discloses a method for the treatment of obstructive sleep apnea and/or snoring comprising the steps of:

identifying an individual that suffers from at least one condition selected from the group consisting obstructive sleep apnea and snoring;

laterally distracting the maxillae of the individual; and maintaining the distraction until a stable state of the maxillae is established.

DESCRIPTION OF THE DRAWINGS

Embodiments of the invention now will be described with reference to the accompanying drawings, in which.

DESCRIPTION OF PREFERRED EMBODIMENTS AND BEST MODE

The rapid maxillary expansion (RME) device, often also referred to as a rapid palatal expander (RPE), has been in use for the purposes of orthodontic treatment for about the last 100 years. Typically it is used where there are crowding or bite problems, occurring for upper jaws that are not as wide as they could or should be. In particular, if there is narrowing of the hard palate there will be constriction of the nasal passages leading to increased nasal resistance.

Figure 1:
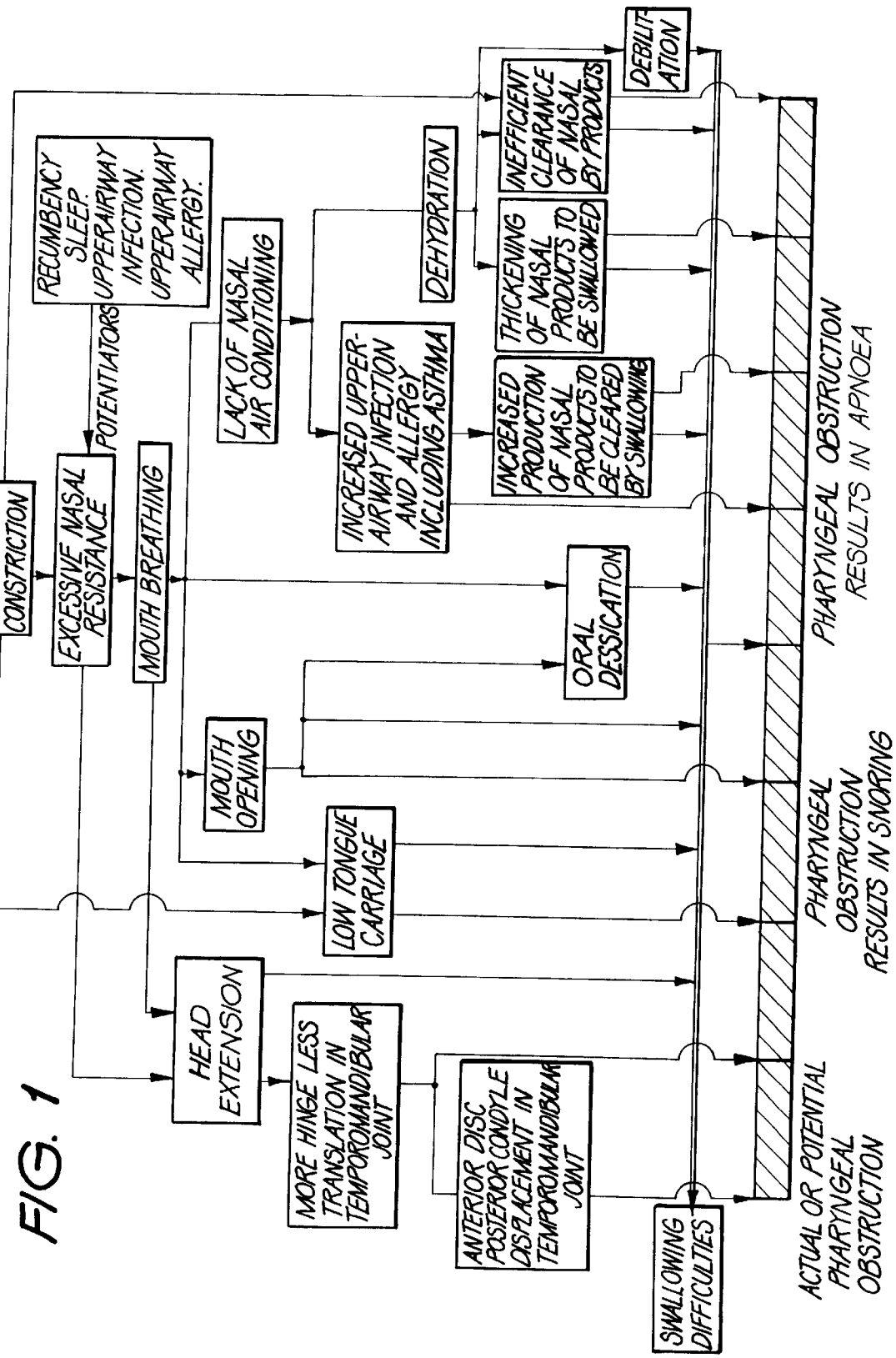
FIG. 1 is the flow diagram discussed above.
Figure 2:
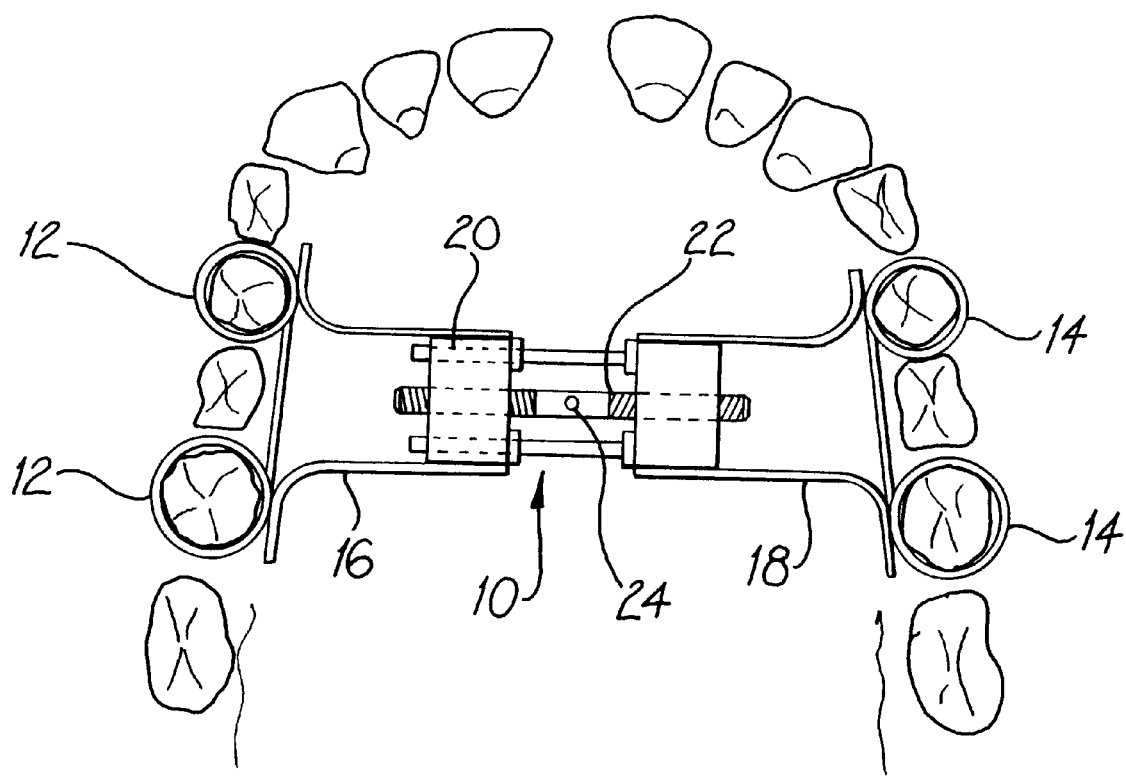
FIG. 2 shows an RME device attached to the upper posterior teeth.

As shown in FIG. 2, a typical RME device 10 comprises two sets of bands 12, 14 surrounding ones of the posterior teeth of the upper jaw. The bands are releasably secured to the respective tooth by an interference fit, or by use of a dental 'adhesive'. Each of the sets is carried on a respective frame 16, 18 to be fastened, typically by soldering, to an intermediate jack or translation screw 20. The central shaft 22 of the jack screw includes two orthogonally arranged bores 24. The jack screw 20 can thus be advanced (or retracted) by the insertion of a rigid pin into one of the bores 24 and by rotation of the shaft 22 through the agency of the pin. A tool suitable for operation of the jack screw 20 is described in U.S. Pat. No. 5,133,659.

Use of the RME device 10 in orthodontic treatments in most cases is commenced in the orthodontist's surgery and without the use of any sedation. In use, therefore, the jack screw 20 is advanced to cause lateral (trans-palatal) forces at pathophysiological levels that usually transcend those that would cause orthodontic movement of teeth through bone. Typically, there is orthopaedic movement of the maxillae and the intermaxillary suture opens (separates). This action also can be understood as a distraction of the maxillae, or alternatively, an expansion of the maxilla, the maxilla being constituted by the two maxillae.

A typical procedure using an RME device in the treatment of OSA and/or snoring consists of an active phase of expansion lasting approximately two weeks, during which about 9 mm of expansion is achieved at the screw 20. This can be achieved by, say, a 2 mm expansion at the screw 20 performed by the orthodontist at the time of fining the RME device 10 followed by a daily 0.5 mm expansion implemented by the patient himself (or by a parent). The procedure can be performed, in most cases, without requiring any form of sedation and without significant discomfort to the patient. The RME device is left in place for approximately 12 weeks, maintaining separation of the maxillae, during which time ossification occurs in the gap 30 formed by separation of the maxillae 32 to reform a normal suture thus stabilising the maxilla. After that 12 week period, the RME device can be easily and painlessly removed, and a conventional orthodontic retainer plate can be fitted and used for an appropriate time. The inventor has discovered that the steps of laterally expanding the maxilla, and maintaining the expansion until a stable state of the maxilla results, not only resolves orthodontic problems, but offers a curative for OSA and snoring where these conditions have as a root cause excessive nasal airway resistance.

Figure 3A:
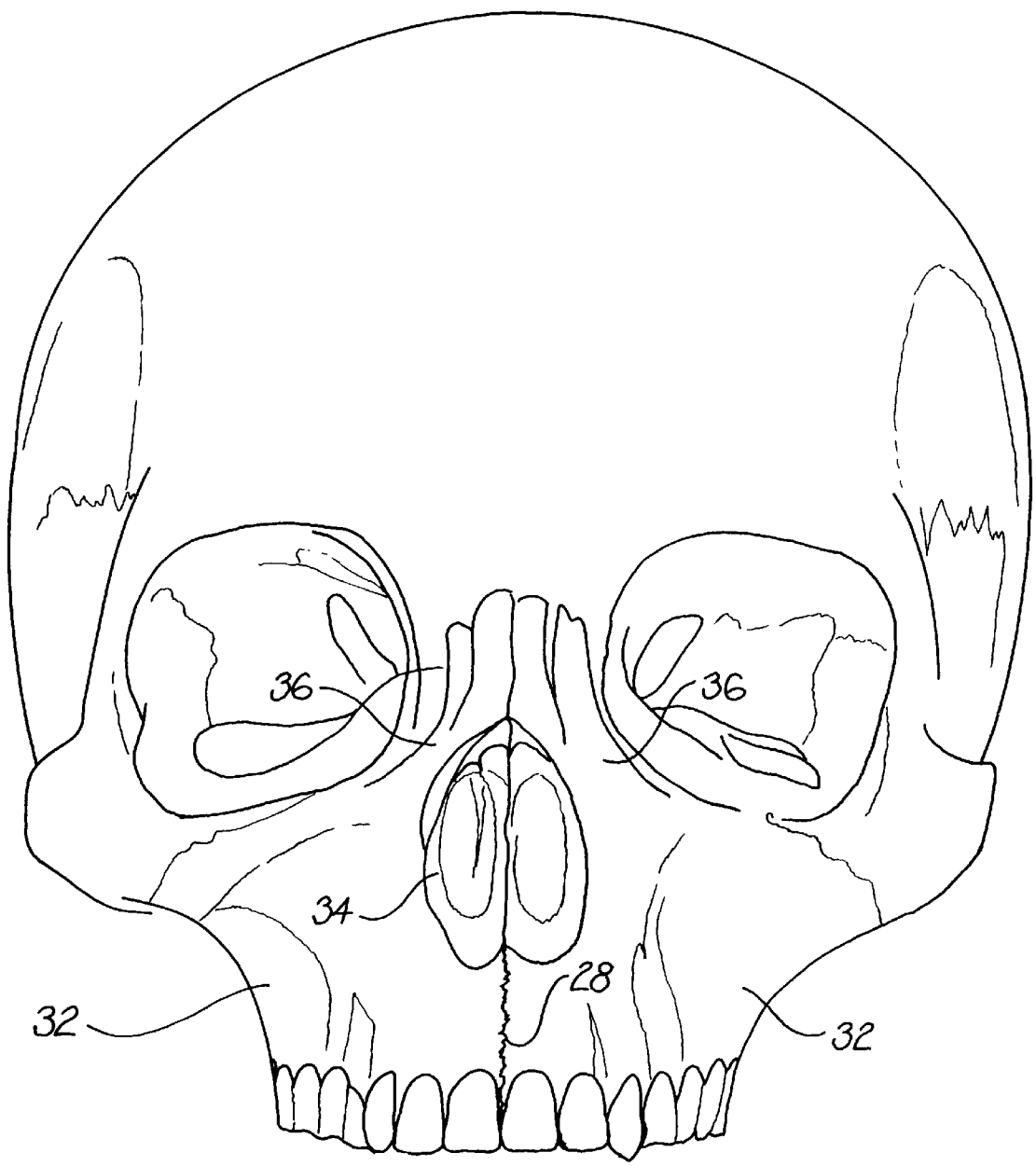
FIGS. 3a and 3b show elevational views of the maxillae before and after separation along the suture.
Figure 3B:
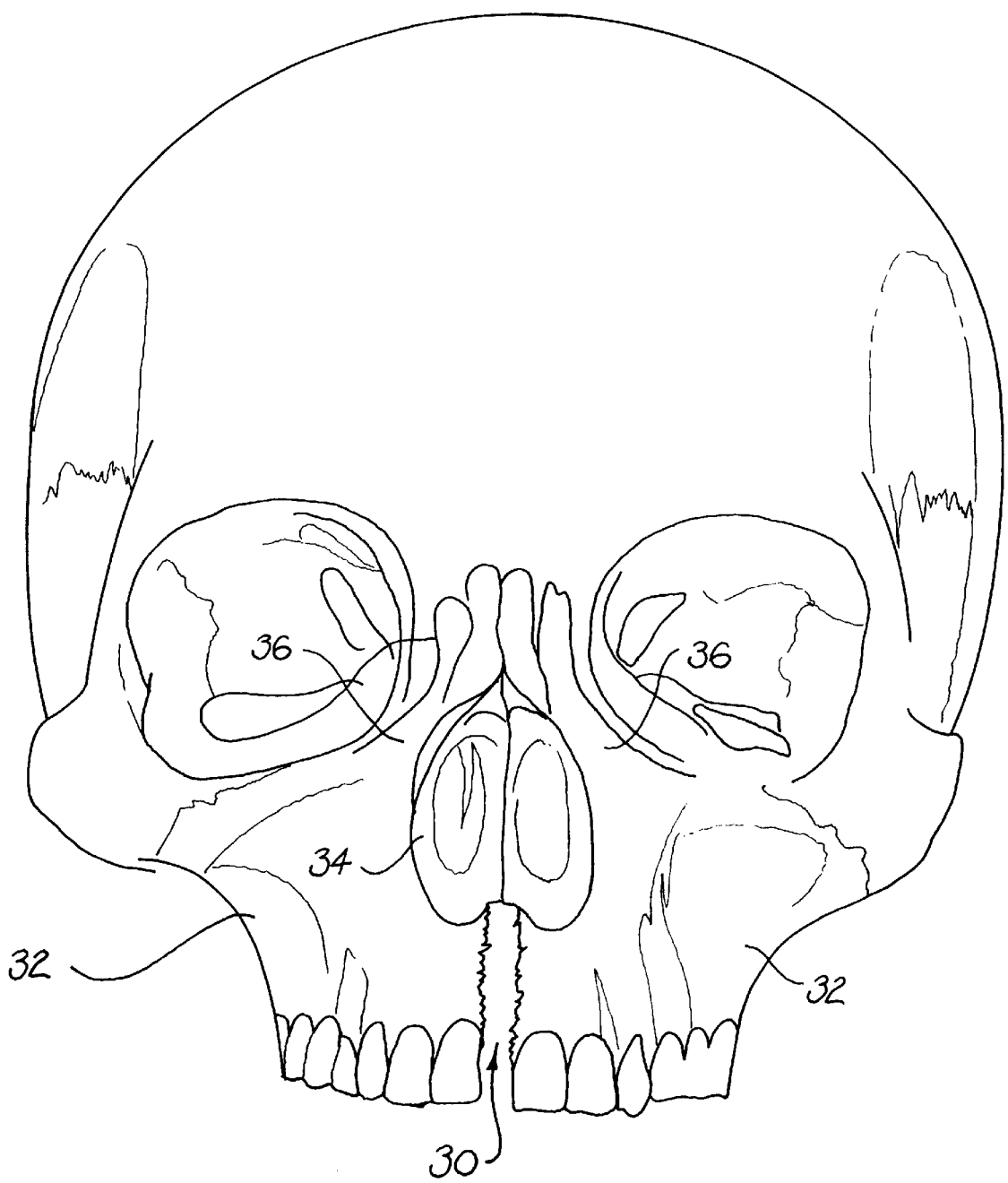

FIG. 3a shows the normal intermaxillary suture 28, while FIG. 3b shows a gap 30 resulting from separation of the intermaxillary suture. The maxillae 32, nasal opening 34 and septum bone 36 also are shown. The nasal opening has a shape approximating an isosceles triangle. By virtue of the expansion, the minimum cross-sectional area of the nasal airway is increased (viz., the base of the triangle is lengthened increasing the area of the triangle). Nasal airway resistance is thereby reduced or normalised.

Figure 4A:
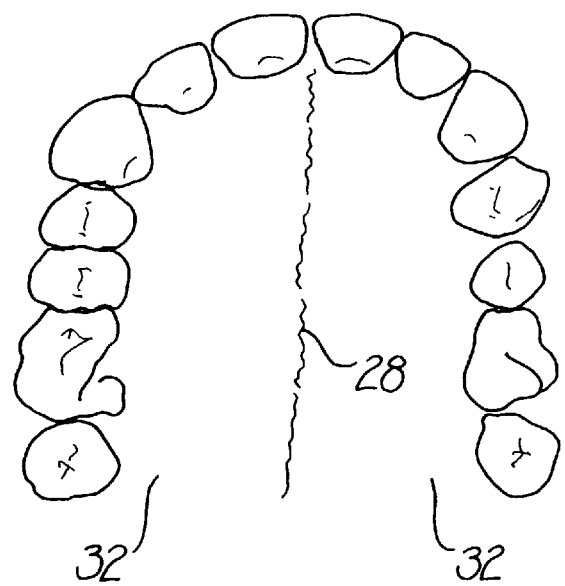
FIGS. 4a and 4b show an underside view of the hard palate.
Figure 4B:
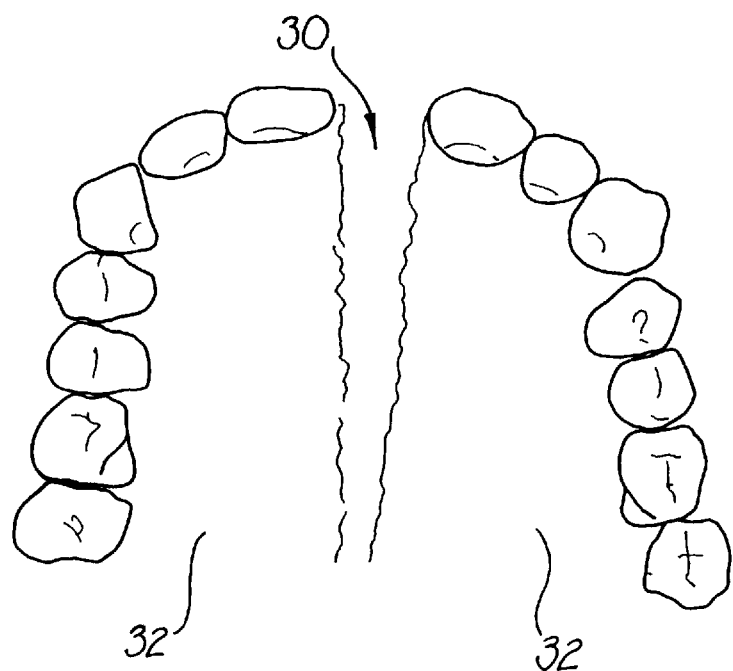

FIG. 4a an underside view of the palatal bones, omitting soft tissue for clarity, particularly identifying the normal suture 28. FIG. 4b is the same view immediately after rapid maxillary expansion has been performed and before new bone growth has occurred.

Not in every case of expansion will a gap occur as shown in FIGS. 3b and 4b, particularly if the rate of expansion matches the rate of new bone growth along the intermaxillary suture 28.

In some circumstances, particularly for patients in their 30's or older, it may be beneficial to perform the technique in conjunction with surgical assistance. There is a buttressing effect via the zygomae that may inhibit orthopaedic movement, thus partial corticotomies of the buccal surfaces of the maxillae are performed, either with or without extension to the piriform aperture or pterygomaxillary fissure, and sometimes with midline labial malletting of an osteotome.

A tabulation of clinical studies, before and after RME treatment, conducted at independent sleep clinics in Sydney, Australia during the period 1994 to early 1996 for the purposes of a reasonable trial in respect of seven patients is shown as follows:

| Patient | Age (yrs) | Baseline AHI | | | AHI after RME | | |
|---|---|---|---|---|---|---|---|
| | | Total | NR | REM | Total | NR | REM |
| 1 | 17 | 7 | 1 | 6 | 0 | 0 | 0 |
| 2 | 23 | 20 | 13 | 74 | 1 | 1 | 4 |
| 3 | 32 | 8 | 4 | 18 | 0 | 0 | 0 |
| 4 | 29 | 8 | 8 | 5 | 2 | 2 | 1 |
| 5 | 24 | 22 | 21 | 30 | 5 | 6 | 1 |
| 6 | 37 | 35 | 30 | 58 | 3 | 2 | 6 |
| 7 | 15 | 7 | 6 | 15 | 4 | 4 | 4 |

"AHI" refers to the well known apnea/hypopnea index, equating to the number of apneas and hypopneas per hour of sleep. "RME" again refers to the rapid maxillary expansion. "NR" is non-rapid eye movement sleep events, whilst "REM" is rapid eye movement sleep events.

As can be noted, there is a profound alleviative and curative effect. The inventor believes a significant percentage of patients suffering OSA and/or snoring can be treated in this manner.

It is clearly the case that the methodologies herein described do not only rely on use of the RME device. Any other equivalent device that operates either magnetically, mechanically, hydraulically or pneumatically to achieve the exertion of trans-palatal force transcending levels that otherwise would cause orthodontic movement of teeth through bone, and instead promote orthopaedic movement of the maxillae can be utilised. Indeed, it may not be necessary to attach such a device to the teeth.

The inventor believes it to be the case that the RME technique is a successful ameliorative or curative treatment also for the other conditions mentioned resulting from excessive nasal airway resistance for reason of clinical observations made by him over 28 years of practise in the performance of about 5000 RME treatments, ostensibly for orthodontic purposes. Excessive mouth breathing, due to increased nasal airway resistance, deprives inhaled air of filtering of airborne pollutants, bacteria, irritants and allergens by the nasal hairs and mucousal lining, and removes the humidifying and warming effects of tee nasal route, contributing to the occurrence of the conditions discussed. Increased nasal airway resistance is resolved by the RME technique.

What is claimed is:

1. A method for the treatment of obstructive sleep apnea and/or snoring comprising the steps of:

identifying an individual that suffers from at least one condition selected from the group consisting of obstructive sleep apnea and snoring;

separating the intermaxillary suture of the individual; and maintaining the separation until a gap formed thereby is occupied by new bone growth and an intermaxillary suture is reformed, resulting in an increased nasal airway volume.

2. The method claim 1, comprising the further step, following said identifying step, of clinically assessing that said individual is a suitable candidate for the treatment of the subsequent steps.

3. The method of claim 2, wherein clinically assessing said individual includes observing that said individual exhibits maxillary constriction.

4. A method for the treatment of obstructive sleep apnea and/or snoring comprising the steps of:

identifying an individual that suffers from at least one condition selected from the group consisting of obstructive sleep apnea and snoring;

securing an expansion device between opposed sides of the upper jaw of the individual;

expanding the expansion device to cause orthopaedic displacement of opposed sides of the upper jaw to achieve separation of the intermaxillary suture; and maintaining the separation until the gap formed thereby is occupied by new bone growth and intermaxillary suture is reformed.

5. A method as claimed in claim 4, comprising the further steps of surgically performing a partial corticotomy of the buccal surfaces of the maxillae with or without extension to the piriform aperture or the pterygomaxillary fissure in conjunction with the step of expanding.

6. A method as claimed in 4, whereby the expansion device is secured to one or more of the posterior teeth on opposed sides of the upper jaw.

7. The method of claim 4, comprising the further step, following said identifying step, of clinically assessing that said individual is a suitable candidate for the treatment of the subsequent steps.

8. The method of claim 7, wherein clinically assessing said individual includes observing that said individual exhibits maxillary constriction.

9. A method for the treatment of the pathophysiological effects of mouth breathing resulting from maxillary constriction, the method comprising the steps of:

laterally expanding the maxilla; and maintaining the maxillary expansion until a stable state of the maxilla is established.

10. A method for the treatment of obstructive sleep apnea and/or snoring comprising the steps of:

identifying an individual that suffers from at least one condition selected from the group consisting of obstructive sleep apnea and snoring;

laterally expanding the maxilla of the individual; and maintaining the maxillary expansion until a stable state of the maxilla is established.

11. The method of claim 10, comprising the further step, following said identifying step, of clinically assessing that said individual is a suitable candidate for the treatment of the subsequent steps.

12. The method of claim 11, wherein clinically assessing said individual includes observing that said individual exhibits maxillary constriction.

13. A method for the treatment of obstructive sleep apnea and/or snoring comprising the steps of:

identifying an individual that suffers from at least one condition selected from the group consisting of obstructive sleep apnea and snoring;

laterally distracting the maxillae of the individual; and maintaining the distraction until a stable state of the maxillae is established.

14. A rapid maxillary expansion device when used to perform the steps of any one of claims 1 to 6 or 9 to 13.

15. The method of claim 13, comprising the further step, following said identifying step, of clinically assessing that said individual is a suitable candidate for the treatment of the subsequent steps.

16. The method of claim 15, wherein clinically assessing said individual includes observing that said individual exhibits maxillary constriction.

17. A method for the treatment of obstructive sleep apnea comprising the steps of:

identifying an individual that suffers from at least one condition selected from the group consisting of obstructive sleep apnea and snoring;

separating the intermaxillary suture of the individual, the separation of the intermaxillary suture being surgically facilitated; and maintaining the separation until a gap formed thereby is occupied by new bone growth and an intermaxillary suture is reformed, resulting in an increased nasal airway volume.

18. The method of claim 17, comprising the further step, following said identifying step, of clinically assessing that said individual is a suitable candidate for the treatment of the subsequent steps.

19. The method of claim 18, wherein clinically assessing said individual includes observing that said individual exhibits maxillary constriction.

20. A method for the treatment of obstructive sleep apnea and/or snoring comprising the steps of:

identifying an individual that suffers from at least one condition selected from the group consisting of obstructive sleep apnea and snoring;

performing and maintaining maxillary expansion on the individual until a stable state of the maxilla and decreased nasal airway resistance are achieved in the individual.

21. The method of claim 20, comprising the further step, following said identifying step, of clinically assessing that said individual is a suitable candidate for the treatment of the subsequent steps.

22. The method of claim 21, wherein clinically assessing said individual includes observing that said individual exhibits maxillary constriction.

23. The method of claim 20, further comprising the step of verifying that the at least one condition has been ameliorated or cured in the individual.

24. The method of claim 20, wherein the identifying step comprises determining whether the individual exhibits greater than or equal to seven AHI events per hour of sleep.

* * * * *